United States Patent [19]

Kaplan et al.

[11] Patent Number: 5,766,550
[45] Date of Patent: Jun. 16, 1998

[54] DISPOSABLE REAGENT STORAGE AND DELIVERY CARTRIDGE

[75] Inventors: Bruce E. Kaplan, Claremont; Piotr M. Swiderski, San Dimas, both of Calif.

[73] Assignee: City of Hope, Duarte, Calif.

[21] Appl. No.: 616,052

[22] Filed: Mar. 14, 1996

Related U.S. Application Data

[63] Continuation-in-part of Ser. No. 404,757, Mar. 15, 1995, abandoned.

[51] Int. Cl.$^6$ .................. G01N 15/06; C07N 21/04; A61K 9/14; C12P 19/34
[52] U.S. Cl. .................. 422/68.1; 424/486; 424/487; 424/501; 514/772.3; 514/772.6; 514/772.4; 524/100; 524/102; 524/103; 935/88; 536/25.3; 435/91.1; 222/478; 222/485; 222/325
[58] Field of Search .................. 422/68.1; 424/486, 424/487, 501; 514/772.3, 772.6, 772.4; 524/100, 102, 103; 985/88; 222/478, 485, 325; 536/25.3; 530/333, 335, 4; 435/91.1

[56] References Cited

U.S. PATENT DOCUMENTS

| | | |
|---|---|---|
| 4,476,017 | 10/1984 | Scharff et al. |
| 4,500,707 | 2/1985 | Caruthers et al. ............ 536/27 |
| 5,262,530 | 11/1993 | Andrus et al. ............ 536/25.31 |
| 5,298,259 | 3/1994 | Lloyd et al. ............ 424/486 |
| 5,324,483 | 6/1994 | Cody et al. |
| 5,429,807 | 7/1995 | Matson et al. |

FOREIGN PATENT DOCUMENTS

| | | |
|---|---|---|
| 305201 | 3/1989 | European Pat. Off. |
| 617047 | 9/1994 | European Pat. Off. |
| 9003383 | 4/1990 | WIPO |
| 9007975 | 7/1990 | WIPO |
| 9301494 | 1/1993 | WIPO |
| 9401213 | 1/1994 | WIPO |

*Primary Examiner*—W. Gary Jones
*Assistant Examiner*—Dianne Rees
*Attorney, Agent, or Firm*—Rothwell, Figg, Ernst & Kurz

[57] ABSTRACT

A disposable cartridge for storage and delivery of reagents for synthesizing and labeling of synthetic oligonucleotides comprises an annular casing, an enclosed area defined by the interior surface of the casing and a non-swellable matrix which is inert to organic solvents is positioned within the enclosed area. Adsorbed onto the surface of the matrix is a reagent to be coupled to an immobilized oligonucleotide precursor. The cartridges can be packaged in such a way as to insure the long-term stability of the reagents contained therein. The cartridge is readily insertable into the reagent delivery line of an automated synthesizer of oligonucleotides and also is useful for the production of labeled oligonucleotides by manual coupling. The cartridges of the invention are disposable after a single use. Substantial economies in the synthesis of labeled synthetic oligonucleotides are achieved by use of the cartridge.

18 Claims, 5 Drawing Sheets

A B C D

DISPOSABLE REAGENT STORAGE AND DELIVERY CARTRIDGE

This application is a continuation-in-part of U.S. Ser. No. 08/404,757, filed Mar. 15, 1995 now abandoned.

FIELD OF THE INVENTION

This invention relates to the synthesis of oligonucleotides. More particularly, the invention provides a disposable cartridge for storage and delivery of reagents useful in automated or manual RNA or DNA synthesis.

BACKGROUND OF THE INVENTION

Standard practice utilizes phosphoramidite chemistry to synthesize oligonucleotides. In this chemistry the nucleotide or other moiety is usually added as the cyanoethyl diisopropylamino phosphoramidite.

The demand for modified or labeled synthetic oligonucleotides is continually increasing. There are multiple reasons for labeling oligonucleotides. Some such uses are:

(i) labeling with fluorescent moieties for sequencing reactions;

(ii) labeling with fluorescent moieties to highlight a biological feature of interest such as might be used to illuminate a particular gene in a technique known as Fluorescent In-Situ Hybridization (FISH);

(iii) labeling of an oligonucleotide to affect its ability to cross or stick to membranes. Examples of such labels including cholesterol, folic acid and pteroic acid; and (iv) labeling of molecules to allow them to stick to a purification medium. Thus, for example, an oligonucleotide labeled with biotin could be purified away from non-biotin-containing oligonucleotides by passage through an avidin column. The biotin-labeled oligonucleotide then could be eluted in a purified state.

Labeling of synthetic oligonucleotides with, for example, biotin, fluorescein and other fluorescent probes is a routine practice. Special phosphoramidites are required for the synthesis of many modified and/or labeled oligonucleotides. These special reagents are usually of the general Formula 1:

wherein F is a label moiety such as a fluorescent label or biotin;

$R_1$ is typically a cyanoethyl group or, if a non-hydrolyzable group is required, then $R_1$ is any alkyl or aryl group, such as ethyl, propyl, phenyl, benzyl or similar moieties; and $R_2$ is typically a diisopropylamino group.

The group F can be any group that a scientist desires to act as a label or reporter molecule. A label or reporter molecule has certain identifying characteristics. It might be fluorescent. The particular fluorescent emission of that moiety might be able to be sensed in a sequencing reaction and allow for localization of the labeled oligonucleotide fragment. The fluorescent moiety, after being connected to a fragment of DNA or RNA might be used as a specific probe in a biological assay. Such an assay might be to localize a particular strand of DNA by hybridization.

The moiety (F) also might be chosen for its ability to bind in a reversible manner to another chemically complimentary moiety. Such a pair might be the biotin-avidin pairing. Another such pairing might be an antigen (peptide) to a particular protein or other biological feature. It also could be a cholesterol-like moiety which might stick to a receptor molecule.

There have been a number of difficulties in the past with using some of these special reagents. Some of these reagents have limited stability in solution. Many also are very expensive, costing up to $3000/g. A 50 mg bottle of special reagent can yield only five or six labeled oligonucleotides when used in an automated mode. Such expensive special phosphoramidites and other reagents for labeling of synthetic oligonucleotides frequently are sold in relatively large (50–100 umol) amounts in 5–15 ml bottles designed to fit the port on the automated synthesizer.

Manufacturers of special phosphoramidite reagents usually recommend use thereof in an automated mode, including automated dilution. The combination of the large dead-volume in most automated oligonucleotide synthesizers and the short term stability of the special reagents in solution makes this automated method wasteful and very expensive.

Modification of a standard automated oligonucleotide synthesis program for manual coupling requires weighing out of the expensive reagent, dilution and introduction of the phosphoramidite reagent with the use of syringes. The consequent inconvenience and loss of reagent from contact with air and moisture makes this technique wasteful and expensive. In addition, a portion of the reagent is lost because of incomplete removal from the bottles in which the reagents are supplied.

Serious losses of the reagent during oligonucleotide synthesis can occur due to:

(i) priming of lines of the automated synthesizer before the beginning of the synthesis;

(ii) material left in the bottle. As noted above, expensive special phosphoramidites frequently are sold in large 5–15 ml. bottles designed to fit the port on the automated synthesizer. After dilution, mixing and delivery a significant amount of material is left on the walls and stopper of the delivery bottle;

(iii) material lost in the delivery lines of the automated synthesizer. Dead volume of those lines is usually 40–60 μl, which is about 10% of the volume of the dissolved labeling reagent. The polytetrafluoroethylene (PTFE) delivery lines also account for losses in labeling reagent because they are permeable to oxygen which is responsible for rapid degradation of phosphoramidite reagents;

(iv) the very short useful lifetime of the reagents, once they are dissolved. Stability in solution of most of them does not exceed 24 hours.

Due to serious limitations in today's software and hardware, automated synthesis of oligonucleotides does not allow for the reduction of the scale of the synthesis below the 0.03 μmole, yielding the purified product in amounts of about $10^{-8}$ mole. Sensitivity of today's fluorescence detection techniques is around $10^{-14}$–$10^{-6}$ mole. Thus, the amount of material produced exceeds the amount required by several thousand times.

OBJECTS OF THE INVENTION

Accordingly, it is an object of this invention to provide methods for synthesizing and labeling oligonucleotides. More specifically, it is an object of this invention to provide such a method which requires significantly smaller amounts of very expensive labeling reagents. Other objects will be apparent from reading the detailed description of the invention, below.

SUMMARY OF THE INVENTION

This invention provides a single use cartridge for the storage and the delivery of reagents, including phosphoramidites, to the reaction cell of an automated synthesizer of oligonucleotides. The use of the cartridge is easily accomplished with today's commercial software and hardware without any additional hardware or changes in the solvents or other reagents on the automated synthesizer. The cartridge comprises an annular casing that contains a non-swellable matrix having adsorbed thereon a preferably predetermined quantity of a reagent to be coupled to an immobilized oligonucleotide precursor. The cartridge is readily available for delivery of the correct amount of reagent to the synthesizer reaction cell upon insertion into the synthesizer's reagent delivery line. It is readily disposable after a single use.

The cartridges of the invention can be safely stored, under appropriately anhydrous conditions, at appropriate temperature, for a substantial time period without significant reagent loss. A plurality of such cartridges, each providing a different reagent and/or different amount of the reagent for use depending upon the desired scale for the synthesis, can be maintained in inventory for use as needed.

GENERAL DESCRIPTION OF THE INVENTION

Figure 1:
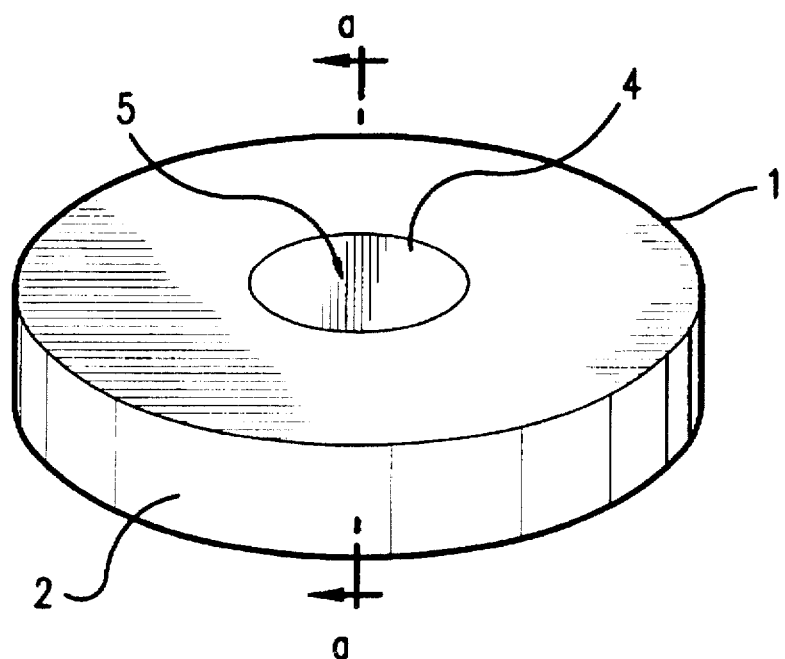
FIG. 1 depicts one form of a cartridge of the invention.
Figure 2:
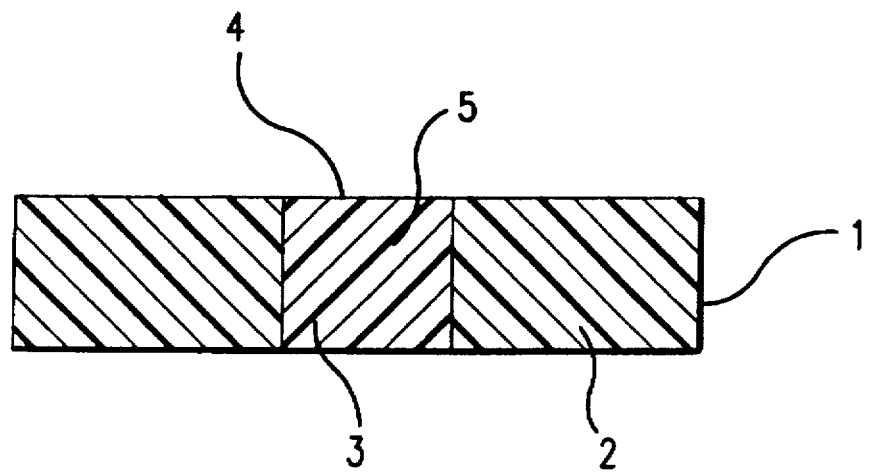
FIG. 2 is a cross-section view of the cartridge taken at the line a—a of FIG. 1.

FIGS. 1 and 2 illustrate an embodiment of the cartridge 1 of the invention which includes an annular casing 2 having an interior surface 3 which defines an enclosed space 4 with a non-swellable matrix 5 positioned therein.

The cartridge casing 2 can be fabricated from any material inert to reagents for the automated synthesis of oligonucleotides. Synthetic resins such as polypropylene, polyethylene, and polytetrafluoroethylene are preferred.

The matrix 5 is fabricated from any material that is non-swellable and inert and/or stable in the presence of oligonucleotide synthesis reagents. The matrix can be porous.

Porosity of the material of the matrix allows for the free flow of liquids through the matrix. The porous matrix will have a thin layer of reagent adsorbed on its surface. The thinner the layer of adsorbed reagent the faster the dissolving/activating/delivery of the reagent to the site of the synthesis of an immobilized oligonucleotide precursor will be. If desired, the matrix material can be provided in the form of beads. The beads need not be porous, as solvent can flow around the beads and dissolve reagent adsorbed on the beads' surface.

The matrix material is selected so as to be non-swellable in organic solvents, particularly in acetonitrile. Acetonitrile is the solvent of choice for dissolving, activating and coupling of reagents in DNA/RNA synthesis. Swelling of the matrix during the loading of the reagent onto the matrix would trap the reagent inside the matrix. Elution of the reagent out of a swellable matrix would require the use of excess liquids that would dilute the expensive reagent and decrease its coupling efficiency. The process of delivery would be much slower and more expensive due to amounts of reagent lost inside the matrix and concomitant decreases in coupling efficiency.

Materials that are most useful as matrix supports are polymers that are hydrophobic. Hydrophobic polymers will have no tendency to absorb water from any source. Water is a general deactivator in phosphoramidite chemistry and is always avoided. Many such hydrophobic matrix materials exist. Examples are polystyrene (highly crosslinked), polyethylene, polypropylene, (polytetrafluoroethylene), or co-polymers of similar nature. Silanized glass wool also can be used as a matrix material. "Highly crosslinked" means a minimum of 8%, preferably between about 8% and about 20%, crosslinking.

The materials discussed above are commercially available. For example,

| Name of Product | Vendor | Catalog # |
| --- | --- | --- |
| TEFLON (polytetrafluoroethylene) Membranes pore size 15 μm | Schleicher & Schuell | TE39 |
| Polypropylene Screen | Small Parts Inc. | A-CMP-74 |
| Bed Support, Polyethylene | Kontes | 420811-2040 |
| Bed Support, PTFE | Kontes | 420809-2040 |
| Bed Support, Polypropylene | Kontes | 420813-0540 |
| Polystyrene Beads Highly Crosslinked | Polymer Laboratories | |

As noted above, the polymers can be fabricated as beads or as porous filter materials. Beads generally are about 200 μm or larger. A preferred matrix comprises beads of polystyrene cross-linked with 8–20% of divinylbenzene. (Polytetrafluoroethylene) also is a suitable support material available in bead form.

The matrix 5 bears or has adsorbed on the surface thereof a preselected reagent to be coupled to an immobilized oligonucleotide precursor. An immobilized oligonucleotide precursor can comprise simply the solid support to which a first selected 5'-protected nucleoside employed in constructing a desired oligonucleotide is attached or a support to which one or more 5'-protected nucleosides have been coupled by stepwise addition in accordance with known procedures. Such reagents include nucleoside phosphoramidites and labeled nucleoside phosphoramidites for use in synthesizing a desired immobilized oligonucleotide precursor and other labeled reagents for labeling synthetic oligonucleotides. Such labeled reagents include those recited above conventionally used to label synthesized oligonucleotides. Thus, a desired label can include moieties such as a fluorescent moiety, biotin, an antigen, a radiolabel, modified nucleoside phosphoramidite, a fluorescein, cholesterol, folic acid or pteroic acid.

As indicated above, such reagents typically are provided as phosphoramidites. Examples of useful reagents include biotin phosphoramidite; 3-nitropyrrole-CE phosphoramidite; fluorescent nucleosides such as etheno-dA-CD phosphoramidite; 7-Deaza-dA-CE phosphoramidite; 3'-dA-CE phosphoramidite; 8-oxo-dG-CE phosphoramidite; methylated nucleosides such as O6-Me-dG-CE phosphoramidite and N6-Me-dA-CE phosphoramidite; convertible dC, dG, dT, dU and dA monomer phosphoramidites such as O4-triazolyl-dT-CE phosphoramidite, O6-phenyl-dI-CE phosphoramidite and S6-DNP-dG-CE phosphoramidite; fluorescein phosphoramidite; 2'-OMe-RNA phosphoramidites such as 2'-OMe-A-CE phosphoramidite and 2'-OMe-C-CE phosphoramidite; halogenated RNA monomers such as Br-U-CE phosphoramidite, 2'-OMe-TMP-5-F-U-CE phosphoramidite, 2'-OMe-2-aminopurine-CE phosphoramidite and 2'-OMe-5-Me-U-CE phosphoramidite. Other useful reagents are well known to persons of skill in the art.

Such materials are commercially available. For example:

| Name of reagent | Vendor | Catalog # |
| --- | --- | --- |
| 6 FAM (6-carboxyfluorescein) | Applied Biosystems | 401-527 |
| TET (4,7,2',7'-tetrachloro-6-carboxyfluorescein) | Applied Biosystems | 401-533 |
| HEX (4,7,2',4',5,7'-hexachloro-6-carboxyfluorescein) | Applied Biosystems | 501-526 |
| Biotin Phosphoramidite | GLEN RESEARCH | 10-1953 |
| Fluorescein Phosphoramidite | GLEN RESEARCH | 10-1963 |
| Biotin Phosphoramidite | BioGenex | BGX 6010 |
| Fluorescein Phosphoramidite | BioGenex | BGX 6008 |
| Biotin-ON Phosphoramidite | Clontech | 5191 |
| Fluorescein Phosphoramidite | Clontech | 5235 |

A selected reagent preferably is provided in a predetermined amount appropriate for the particular addition reaction of interest, e.g., for the coupling of a particular label (such as biotin or a fluorescent label) to an immobilized synthesized oligonucleotide precursor. This invention will allow for using approximately just one milligram of a specific labeling reagent per synthesis of labeled oligonucleotide. Thus, the use of special reagents is more affordable. The device also allows each laboratory to prepare its own labeled oligonucleotides without opening a new bottle of labeling reagent for each synthesis. Very often an experiment will require a multiplicity of labels but only one of each label per oligonucleotide. At present one would have to use a bottle of special reagent to prepare 1–5 oligonucleotides. Any reagent not used in one day is wasted and the real cost thus can be as high as the cost of one bottle of reagent per oligonucleotide. With the device of this invention, the labeling of an oligonucleotide requires one cartridge. Thus, this device decreases the amount of reagent consumed from the present high of 50 mg for one oligonucleotide (this would be the case if one wanted to label only one oligonucleotide and the rest of the reagent were wasted) to as little as 1 mg per oligonucleotide. With the method of this device the amount of material produced is still several thousand times more than required for many of their uses.

The reagent-containing cartridges can be made using any of a number of conventional procedures for adsorbing a substance onto a matrix. Four examples are indicated below:

1. The reagent can be adsorbed on the surface of a membrane matrix support. The reagent first is dissolved in an inert solvent, such as acetonitrile, and dispensed onto the membrane matrix support. All operations are carried out in an inert atmosphere to exclude water and oxygen. The membrane matrix support could already be in the cartridge holder or the membrane could be placed in the holder after the adsorption of the reagent. The solvent is removed under vacuum or by evaporation in an inert gas atmosphere.
2. The reagent can be adsorbed on the surface of a matrix support. The reagent is first dissolved in an inert solvent, such as benzene, and dispensed onto the matrix support. All operations are carried out in an inert atmosphere to exclude water and oxygen. The membrane matrix support could already be in the cartridge holder of the membrane could be placed in the holder after the adsorption of the reagent. The solvent is removed by lyophilization under vacuum.
3. The reagent can be adsorbed, in a bulk fashion, onto the surface of beads. The reagent is first dissolved in an inert solvent, such as acetonitrile, and dispensed onto the beads. The solvent is removed under vacuum or by the passage of an inert gas. All operations are carried out in an inert atmosphere to exclude water and oxygen. The beads of the matrix then are apportioned into cartridges with one filter in place. A second filter then is added so that the beads are not washed into the reaction chamber and the lines of the synthesizer.
4. The cartridges to be loaded can be prepared with the beads in between two filters. The appropriate amount of reagent, predissolved in an inert solvent, is added to each cartridge. Solvent, such as acetonitrile or benzene, is removed by lyophilization under vacuum or by evaporation with an inert gas. All operations are carried out in an inert atmosphere to exclude water and oxygen.

Figure 3:
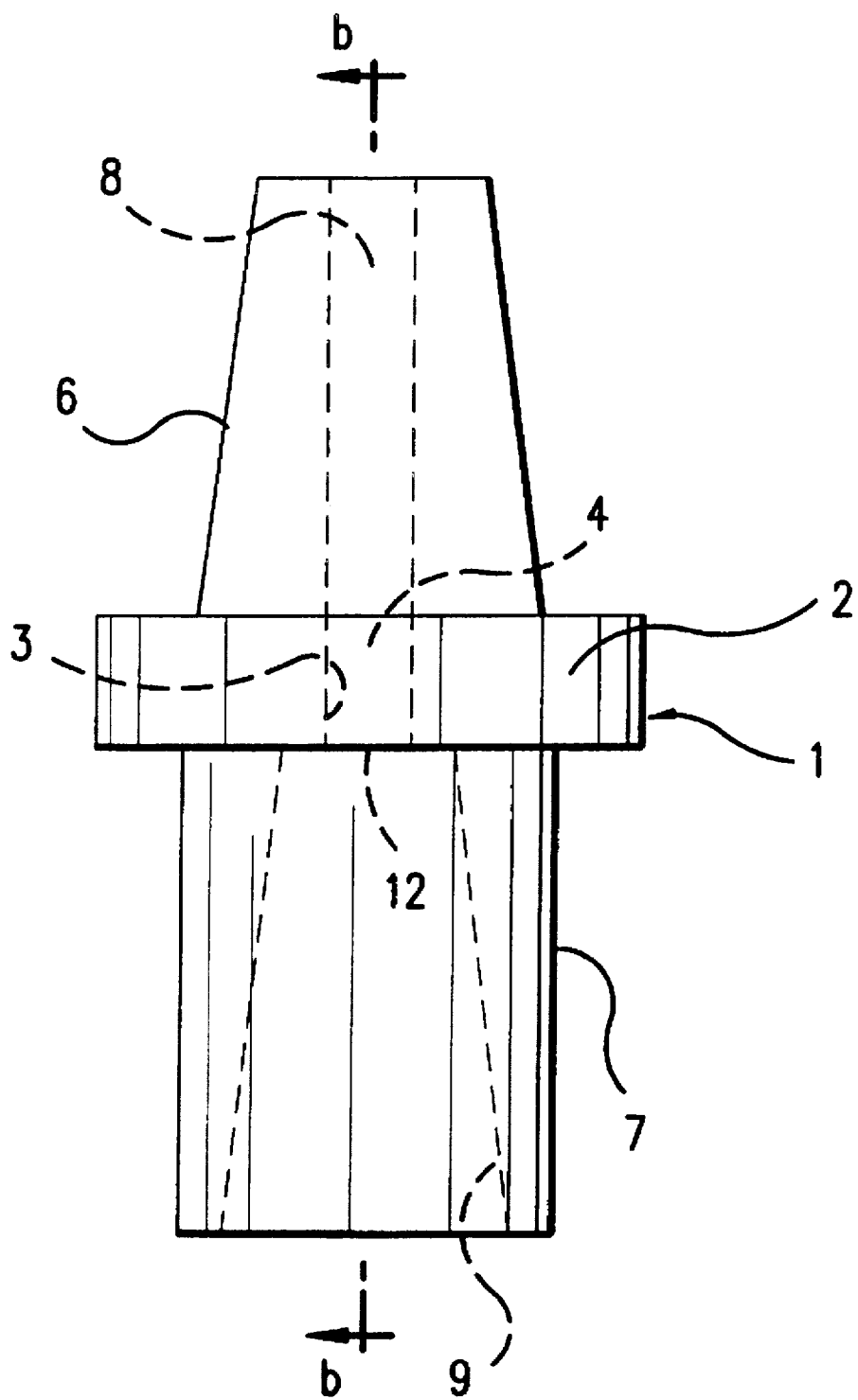
FIG. 3 depicts a cartridge of the invention provided with means such as luer fittings for insertion into the reagent delivery line of an oligonucleotide synthesizer. Other fittings also could be used.
Figure 4:
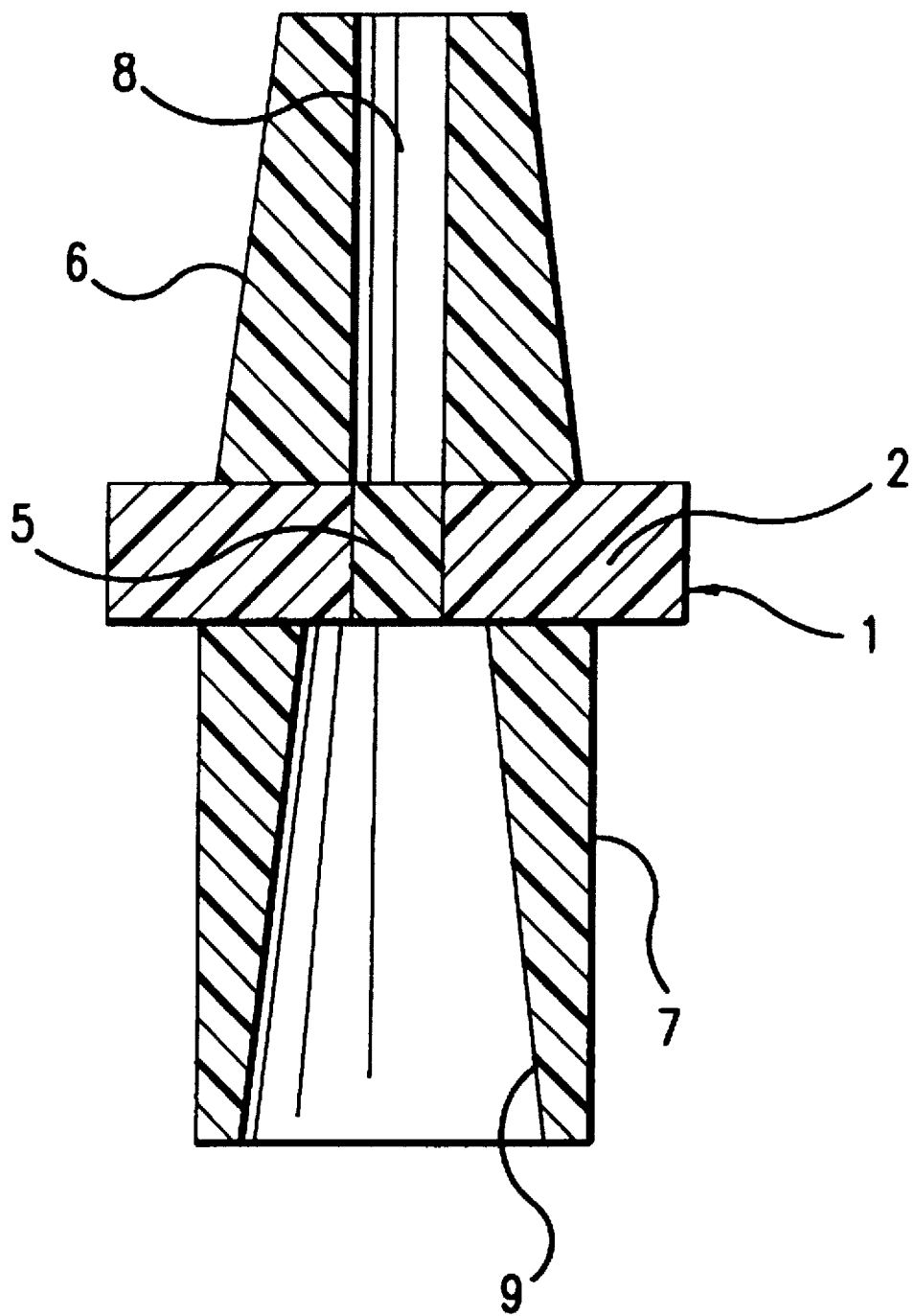
FIG. 4 is a cross-sectional view of the cartridge as shown by FIG. 3 taken on the line b—b.

The cartridges of the invention preferably are provided with means such as luer locks, luer fittings or threaded fittings for ready incorporation into the reagent delivery line of an oligonucleotide synthesizer. In the preferred embodiments of the invention, the cartridge and fitting elements are molded as a unitary structure from an appropriate synthetic resin. Such a unitary device is depicted by FIGS. 3 and 4. Referring to these figures, a cartridge 1 is disposed between an upper luer fitting 6 and a lower luer fitting 7. The upper fitting 6 includes a fluid passage 8 in fluid flow communication with the reagent bearing matrix 5 in the casing 1. The lower fitting includes a fluid passage 9 positioned to receive fluids passing through the reagent containing matrix 5 and conduct such fluids to the reagent cell of an oligonucleotide synthesizer.

Figure 5:
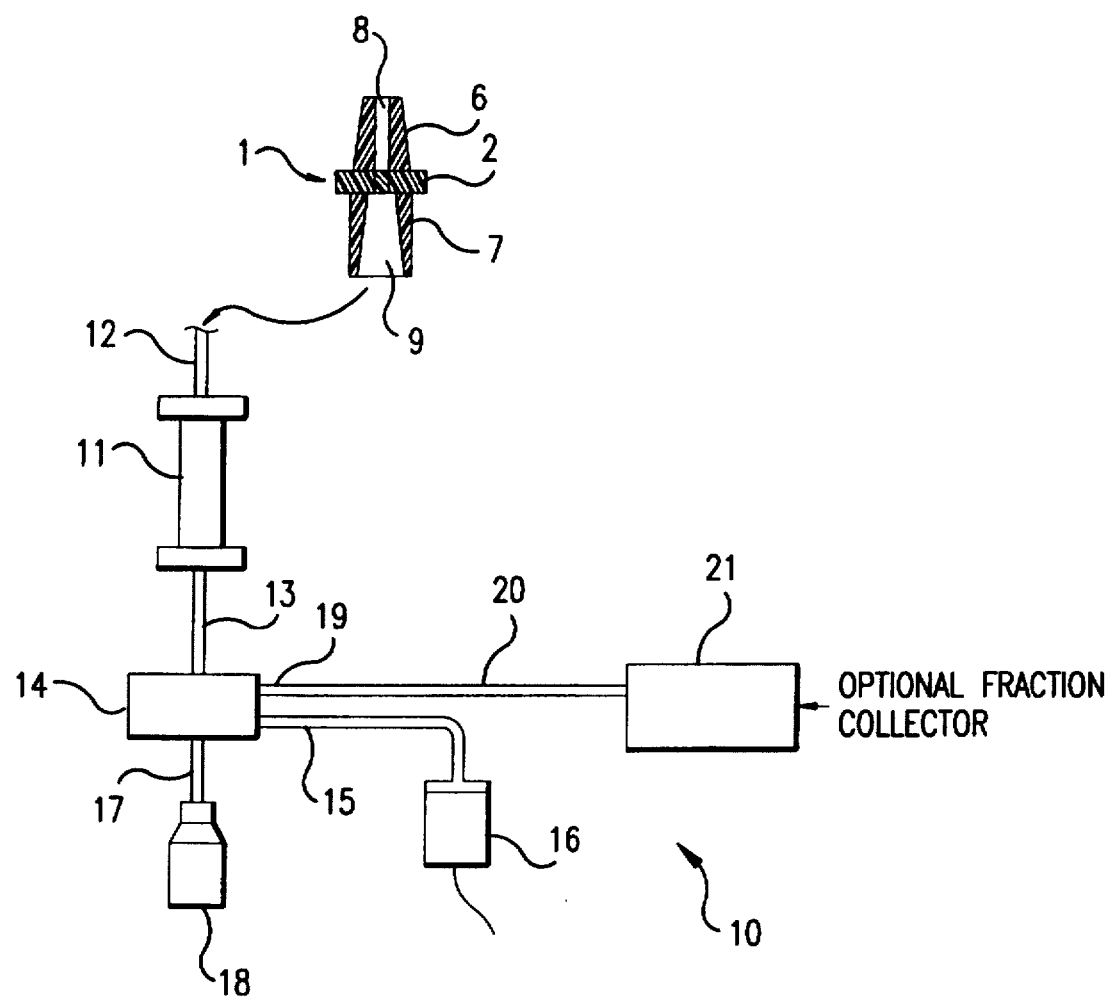
FIG. 5 is a schematic depiction of a portion of a DNA/RNA synthesizer, including the reaction cell and the cartridge of the invention located in the delivery line to accommodate delivery of a reagent to the reaction cell in which the desired oligonucleotide is synthesized on a solid support.

Schematic FIG. 5 depicts a portion of an oligonucleotide synthesizer, a cartridge 1 having fitting 6 and 7 shown encircled. The synthesizer 10 includes a reaction cell or column 11 having a line 12 for the introduction of reagents. The cartridge 1 is fitted into the line 12 before the reaction cell or column 11.

The cell or column 11 is connected by line 13 to T-block 14 that is provided with an oligonucleotide collection port 15 and collection vial 16, and a waste port 17 and waste bottle 18. The T-block has a trityl collection port 19 connected by line 20 to optional fraction collector 19.

Cartridges of the invention are useful in conjunction with known forms of software for automated synthesizers of oligonucleotides. In such use, the oligonucleotide is synthesized in the DMT-OFF mode. An appropriate cartridge is positioned below the reaction cell of the synthesizer and a commercially available program is run. Preferably, such a program delivers the appropriate amount of an activator such as tetrazole or 5-(ethylthio)-1H-tetrazole in acetonitrile or similar solvent through the porous matrix of the cartridge to the reaction cell. The oligonucleotide synthesis proceeds in routine fashion. Unreacted sites are capped, if necessary. Trivalent phosphorous, if present, is oxidized or thiolated to the pentavalent form. Appropriate washing with acetonitrile or similar solvent is accomplished at appropriate times.

For use in manual coupling procedures, the oligonucleotide is also synthesized in the DMT-OFF mode. The reaction cell is blown dry with argon. A cartridge of the invention is positioned below the reaction cell, filled by means of a dry syringe with an appropriate activator, e.g., 0.40–0.45M tetrazole in acetonitrile, preferably in an amount equal to the dead volume of the cell and cartridge. Dead volume of the cell and cartridge should be similar. Typical cell volumes are 50–100 μL and the internal volume of the cartridge will be about 50 μL. The activator solution is delivered slowly to the cell to dissolve, activate and deliver the reagent. Thereafter, unreacted sites are capped, if necessary, and trivalent phosphorus, if present, is converted to pentavalent phosphorous by oxidation or thiolation. Appropriate washing, e.g., with acetonitrile or similar solvent is accomplished where appropriate between these steps.

A prototype cartridge of the invention in which the matrix was silanized glass wool on which T-amidite was adsorbed was successfully utilized. Eight milligrams of the T-amidite were delivered to the reaction cell. The coupling yield was 87%.

Example I

This experiment was designed to briefly compare two techniques: delivery of amidite by a Single Use Disposable Cartridge and fully automated technique of delivery utilizing a DNA Synthesizer 394 from Applied Biosystems.

1. A loaded cartridge as shown generally by FIG. 4 was prepared by placing 1 mg of 6-FAM-amidite (6carboxyfluorescein-amidite). (Applied Biosystems) adsorbed onto silanized glass wool in the device having Luer fittings on both ends. Synthesis of oligomer was performed in the DMT-off mode followed by a one-minute acetonitrile wash and one minute reverse flush (nitrogen drying cycle). After that the cartridge was placed underneath the cell. Lines were filled with activator prior to the delivery of activator (tetrazole, 0.45M in acetonitrile). Solution of tetrazole/activator was delivered for 3.2 s (four periods of 0.8 s separated by 30 s of WAIT) which is enough to dissolve/activate/deliver the 6-FAM-amidite to the cell.

The dissolved/activated/delivered 6-FAM-amidite (6-carboxyfluorescein-amidite). (Applied Biosystems) was left inside the cell for three minutes to complete the coupling reaction. The reaction cycle was completed by 20 s of oxidation on the synthesizer.

2. Automated synthesis was performed the usual way by placing the 6-FAM-amidite (6-carboxyfluorescein-amidite) on the port #5 of the synthesizer, the HEX-amidite (4, 7, 2', 4', 5,'7'-hexachloro-6-carboxyfluorescein-amidite). (Applied Biosystems) on the port #6, diluting and priming on the synthesizer.

The HEX-amidite (4, 7, 2', 4', 5, '7'-hexachloro-6-carboxyfluorescein-amidite) and 6-FAM-amidite (6-carboxyfluorescein-amidite) fluorescent amidites from Applied Biosystems utilized in this experiment do not have the DMT-protection attached. Estimation of yield of reaction is difficult and therefore is not reported.

|  | Disposable Cartridge | Symbol | Automated Synthesis | Symbol |
|---|---|---|---|---|
| HEX-22-mer (4,7,2',4',5,'7'-hexachloro-6-carboxyfluorescein-amidite) | 12 ODU (A260) | A | 31 ODU (A260) | B |
| 6-FAM-21-mer | 11 ODU (A260) | C | 25 ODU (A260) | D |

Figure 6:
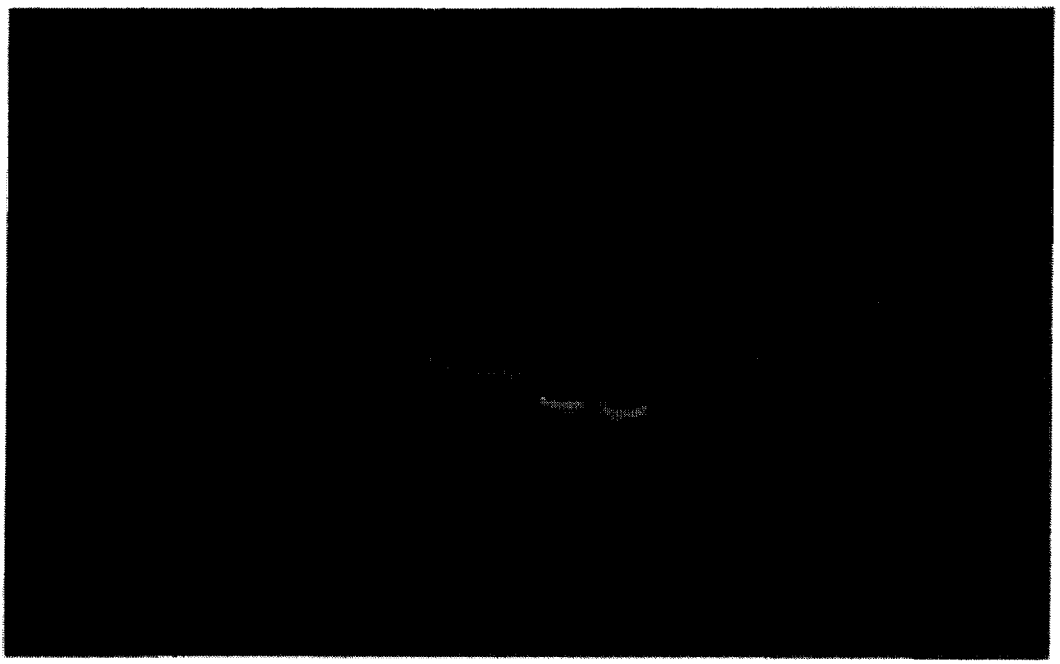
FIG. 6 is a photograph of a polyacrylamide electrophoresis gel showing labeled oligonucleotides prepared by the method of the present invention and by a conventional method.

Both products were cleaved and processed following the recommendations of Applied Biosystems. Products were visualized by analytical polyacrylamide electrophoresis (PAGE). Products obtained from both experiments are identical. See FIG. 6. Although the yield was not as high when using the cartridge method the amount of material produced was still several thousand times more than required for their use.

We claim:

1. A device comprising
   (a) an annular casing;
   (b) an enclosed area defined by the interior surface of said annular casing;
   (c) a matrix positioned within said enclosed area, wherein said matrix is non-swellable and insoluble and stable in an organic solvent; and
   (d) adsorbed on the surface of the matrix a reagent to be coupled to an immobilized oligonucleotide precursor.

2. The device of claim 1, wherein the reagent comprises a label.

3. The device of claim 2, wherein the reagent comprises a labeled phosphoramidite.

4. The device of claim 2, wherein the label comprises a fluorescent moiety, biotin, an antigen, a radiolabel, fluorescein, cholesterol, folic acid, pteroic acid or a modified phosphoramidite.

5. The device of claim 1, wherein the matrix comprises a hydrophobic polymer.

6. The device of claim 1, wherein the matrix comprises highly crosslinked polystyrene, polyethylene, polypropylene, TEFLON (polytetrafluoroethylene) or silanized glass wool.

7. The device of claim 1, wherein the polymeric matrix comprises polystyrene highly crosslinked with divinylbenzene.

8. A device for storing and dispensing a reagent to be coupled to an immobilized oligonucleotide precursor for use in an automated synthesizer of oligonucleotides having a reagent delivery line and a reaction cell, said device comprising:
   (a) an annular casing;
   (b) an enclosed area defined by the interior surface of said annular casing;
   (c) a non-swellable polymeric matrix inert to solvents and reagents used in automated synthesis of oligonucleotides positioned within said enclosed area, wherein said matrix has uniformly adsorbed onto the surface thereof a predetermined amount of a reagent to be coupled to an immobilized oligonucleotide precursor;
   (d) means for fluid connection of said enclosed area of said casing with said reagent delivery line of said automated synthesizer; and
   (e) means for fluid connection of said enclosed area of said casing to said reaction cell of said automated synthesizer, wherein said device provides a passage for the flow of fluid sequentially through said synthesizer reagent delivery line, said matrix positioned within said enclosed area of said annular casing and thereafter into said reaction cell of said synthesizer.

9. In an automated synthesizer of oligonucleotides, said synthesizer having a line for delivery of reagents to a reaction cell, the improvement which comprises a storage and dispensing device positioned within said delivery line, wherein positioned within said device is a matrix which is non-swellable and insoluble and stable in organic solvents and adsorbed on the surface of said matrix is a reagent to be coupled to an immobilized oligonucleotide precursor within said reaction cell.

10. A unitary, disposable, single use storage and delivery device comprising (a) a chamber defined by an annulus;

(b) a polymeric matrix which is non-swellable in organic solvents positioned within said chamber;

(c) a predetermined quantity of a reagent to be coupled to an immobilized oligonucleotide precursor adsorbed on said matrix;

wherein said reagent has been pre-selected to achieve a specific coupling to said immobilized oligonucleotide precursor and said predetermined quantity of said reagent is a quantity required to achieve said specific coupling; and (d) said chamber is positioned between upper and lower means for fluid connection of said device to a reagent supply line of an automated oligonucleotide synthesizer.

11. The device of claim 10, wherein said upper and lower means for fluid connection are luer fittings or luer locks or threaded fittings.

12. The device of claim 10, wherein said polymeric matrix is a highly crosslinked polymer.

13. The device of claim 12 wherein the matrix is in the form of beads.

14. The device of claim 10, wherein said matrix comprises a polystyrene, polyethylene, polypropylene or silanized glass wool.

15. The device of claim 14, wherein said matrix comprises a polystyrene highly crosslinked with divinylbenzene.

16. The device of claim 10, wherein said reagent comprises a label.

17. The device of claim 16, wherein said reagent comprises a labeled phosphoramidite.

18. The device of claim 16, wherein said label comprises a fluorescent moiety, biotin, an antigen, a radiolabel, fluorescein, cholesterol, folic acid, pteroic acid or a modified phosphoramidite.

* * * * *